US012755255B2

(12) United States Patent
Frischkorn et al.

(10) Patent No.: US 12,755,255 B2
(45) Date of Patent: Oct. 6, 2026

(54) METHOD OF OBTAINING INFORMATION ON THE RECYCLABILITY OF AT LEAST ONE FLEXIBLE FOAM MADE AT LEAST PARTIALLY OF AT LEAST ONE POLYURETHANE

(71) Applicants: TRINAMIX GMBH, Ludwigshafen Am Rhein (DE); BASF POLYURETHANES GMBH, Lemfoerde (DE); BASF SE, Ludwigshafen am Rhein (DE)

(72) Inventors: Sebastian Frischkorn, Ludwigshafen am Rhein (DE); Robert Lovrincic, Ludwigshafen am Rhein (DE); Patrick Weiss, Lemfoerde (DE); Christoph Schnorpfeil, Ludwigshafen am Rhein (DE)

(73) Assignees: TRINAMIX GMBH, Ludwigshafen am Rhein (DE); BASF POLYURETHANES GMBH, Lemfoerde (DE); BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 18/880,871

(22) PCT Filed: Jul. 25, 2023

(86) PCT No.: PCT/EP2023/070529

§ 371 (c)(1),
(2) Date: Jan. 3, 2025

(87) PCT Pub. No.: WO2024/023064

PCT Pub. Date: Feb. 1, 2024

(65) Prior Publication Data

US 2025/0245632 A1 Jul. 31, 2025

(30) Foreign Application Priority Data

Jul. 26, 2022 (EP) .................................... 22186826

(51) Int. Cl.
*G06Q 10/30* (2023.01)
*C08G 18/32* (2006.01)
(Continued)

(52) U.S. Cl.
CPC ......... *G06Q 10/30* (2013.01); *C08G 18/3206* (2013.01); *G16C 20/20* (2019.02); *C08G 2101/00* (2013.01)

(58) Field of Classification Search
CPC ............ G06Q 10/30; B29B 2017/0203; B29B 2017/0279; B29B 17/02; Y02W 30/20; Y02W 30/62
See application file for complete search history.

(56) References Cited

U.S. PATENT DOCUMENTS

2008/0190819 A1* 8/2008 Schlummer ............... B03B 5/28 209/172.5
2022/0005002 A1* 1/2022 Graf von Stauffenberg ................ G07F 7/06
2024/0264078 A1* 8/2024 Rubio Moreno ....... B07C 5/342

FOREIGN PATENT DOCUMENTS

EP 3957453 A1 2/2022
EP 3656525 B1 11/2023

OTHER PUBLICATIONS

Pieszczek, L., and M. Daszykowski. "Improvement of recyclable plastic waste detection—A novel strategy for the construction of rigorous classifiers based on the hyperspectral images." Chemometrics and Intelligent Laboratory Systems 187 (2019): 28-40. (Year: 2019).*

(Continued)

*Primary Examiner* — Scott M Tungate
(74) *Attorney, Agent, or Firm* — Armstrong Teasdale LLP

(57) ABSTRACT

Disclosed herein is a computer-implemented method of obtaining information on the recyclability of at least one flexible foam made at least partially of at least one polyurethane.

Further disclosed herein are a computer program and a computer-readable storage medium for performing the method, a method of treatment of the flexible foam, a device for obtaining information on the recyclability of the flexible foam and a system for treatment of the flexible foam.

20 Claims, 3 Drawing Sheets

(51) Int. Cl.
*G16C 20/20* (2019.01)
*C08G 101/00* (2006.01)

(56) References Cited

OTHER PUBLICATIONS

International Search Report for PCT/EP2023/070529 dated Sep. 14, 2023, 3 pages.
Written Opinion for PCT/EP2023/070529 dated Sep. 14, 2023, 8 pages.

* cited by examiner

METHOD OF OBTAINING INFORMATION ON THE RECYCLABILITY OF AT LEAST ONE FLEXIBLE FOAM MADE AT LEAST PARTIALLY OF AT LEAST ONE POLYURETHANE

CROSS-REFERENCE TO RELATED APPLICATIONS

This application is a U.S. National Phase Application of International Patent Application No. PCT/EP23/70529, filed Jul. 25, 2023, which claims priority to European Patent Application No. 22186826.8, filed Jul. 26, 2022, each of which are hereby incorporated by reference herein.

TECHNICAL FIELD

The invention relates to a computer-implemented method of obtaining information on the recyclability of at least one flexible foam made at least partially of at least one polyurethane, to a device for obtaining information on the recyclability of at least one flexible foam made at least partially of at least one polyurethane and to a computer program and a computer-readable storage medium for performing said method. The invention further relates to a method and a system of treatment of at least one flexible foam made at least partially of at least one polyurethane. The methods and devices may specifically be used in the field of recycling. As an example, the methods and devices may be used for sorting multicomponent flexible foams prior to a recycling process. However, other fields of applications are also feasible.

BACKGROUND ART

Flexible foams, specifically flexible foams comprising polyurethane, for example polyurethane mattresses or other foam material, such as upholstered furniture, generally have a high intrinsic material value. Thus, recycling of these flexible foams may be desirable due to economic and/or environmental reasons. Typically, recycling of the flexible foams is done via chemical recycling processes. In such processes, the material of the flexible foam may be separated into its chemical constituents. For example, flexible foams comprising polyurethane may be separated into their specific isocyanate constituent, such as a toluene diisocyanate isomer (TDI) or a methylene diphenyl diisocyanate isomer (MDI), and into their specific polyol constituent, such as a standard polyol, a high-resiliency (HR) polyol or the like. The chemical recycling process is typically optimized for a specific combination of polyol and isocyanate of the polyurethane. Thus, flexible foams comprising polyurethane need to be sorted according to their specific composition prior to the chemical recycling process. Furthermore, other additives, such as flame retardants, for example melamine or expandable graphite, or other filler compounds, for example styrene-acrylonitrile, may cause problems during the chemical recycling process and need to be identified prior to the recycling process.

As an example, EP 3 957 453 A1 discloses a method for separating waste polyurethane foams. At least one respective spectrum is recorded for each polyurethane sample of a supply stream comprising polyurethane samples from waste. The at least one respective spectrum is recorded by near-infrared spectroscopy. Each polyurethane sample of the supply stream is classified by a classification algorithm, which classification algorithm is based on machine learning, based on the respective at least one spectrum into a respective class of at least two classes. The supply stream comprising polyurethane samples is separated into at least two streams according to the classification into the respective class. Each class corresponds to a type of polyurethane. Further, a system for separating waste polyurethane foams is also disclosed.

EP 3 656 525 A1 discloses a process for manufacturing a single-material polyurethane or latex web from recycled mattresses, said process comprising the following successive steps: a) a step of dismantling used mattresses, making it possible to provide separate base materials, the base materials comprising in particular polyurethane foams and latex foams; b) a step of selecting uncontaminated polyurethane, respectively latex foams; c) a step of grinding said foams obtained in step b), to obtain uncontaminated polyurethane or latex foam flakes with an average particle size of 20 mm or less; d) a step for forming a polyurethane or latex monomaterial web, comprising mixing the polyurethane or latex foam flakes from step d) with a binder. The invention is useful for making mattresses and upholstery.

Despite the advantages achieved by known methods and devices, several technical challenges remain. Specifically, there is still a need for an accurate and reliable sorting of flexible foams comprising polyurethane prior to the chemical recycling process.

PROBLEM TO BE SOLVED

It is therefore desirable to provide methods and devices which at least partially address above-identified technical challenges. Specifically, methods and devices shall be proposed which allow for an accurate and reliable sorting of flexible foams comprising polyurethane.

SUMMARY

This problem is addressed by a computer-implemented method of obtaining information on the recyclability of at least one flexible foam made at least partially of at least one polyurethane, a device for obtaining information on the recyclability of at least one flexible foam made at least partially of at least one polyurethane, a computer program and a computer-readable storage medium for performing said method and by a method and a system for treatment of at least one flexible foam made at least partially of at least one polyurethane with the features of the independent claims. Advantageous embodiments which might be realized in an isolated fashion or in any arbitrary combinations are listed in the dependent claims as well as throughout the specification.

In a first aspect of the present invention, a computer-implemented method of obtaining information on the recyclability of at least one flexible foam made at least partially of at least one polyurethane is disclosed.

The term "computer" as used herein is a broad term and is to be given its ordinary and customary meaning to a person of ordinary skill in the art and is not to be limited to a special or customized meaning. The term specifically may refer, without limitation, to a device or to a combination or network of devices having at least one data processing means, such as at least one processing unit, also referred to as a processor. The computer, additionally, may comprise one or more further components, such as at least one of a data storage device, an electronic interface or a human-machine interface.

The term "computer-implemented" as used herein is a broad term and is to be given its ordinary and customary meaning to a person of ordinary skill in the art and is not to be limited to a special or customized meaning. The term specifically may refer, without limitation, to a process involving at least one computer and/or at least one computer network, such as a plurality of interconnected computers. The computer and/or computer network may comprise at least one data processing means which is configured for performing the process, such as at least one of the method steps of the computer-implemented method. Specifically, each one of the method steps of the computer-implemented method may be performed by using the computer and/or computer network. The method steps may at least partially be performed automatically, specifically without user interaction.

The term "obtaining" as used herein is a broad term and is to be given its ordinary and customary meaning to a person of ordinary skill in the art and is not to be limited to a special or customized meaning. The term specifically may refer, without limitation, to a process of at least one of generating, determining and retrieving at least one item of information, specifically the information on the recyclability of the flexible foam. The process of obtaining the item of information may comprise a step-wise process, specifically comprising one or more determination steps and one or more decision steps, as will be outlined in further detail, for example in the form of a decision tree. The decision tree may comprise one or more levels according to a number of decision steps being performed in the process of obtaining the item of information. Specifically, the decisions steps may represent a decision node in the decision tree. At each decision node of the decision tree, two or more possible outcomes may be given. Thus, the process of obtaining the item of information may be a multi-step process, specifically comprising multiple decisions to be taken to generate and/or determine the item of information. The item of information may specifically be the information on the recyclability of the flexible foam.

The term "information on the recyclability" as used herein is a broad term and is to be given its ordinary and customary meaning to a person of ordinary skill in the art and is not to be limited to a special or customized meaning. The term specifically may refer, without limitation, to any item of information related to a recycling process, specifically to a chemical recycling process. The information on the recyclability may be a numerical and/or an alphanumerical item of information on the recyclability. For example, the information on the recyclability may be a binary item of information, in particular indicating the recyclability or the non-recyclability of a specific material or object, such as by one or more pre-determined recycling processes. The information on the recyclability may be a broad item of information, specifically comprising one or more items of information on the recyclability. The information on the recyclability may comprise an item of information indicating a suitability of a material or object of being subjected to a recycling process, specifically to a chemical recycling process, such as "recyclable" or "non-recyclable". Additionally or alternatively, the information on the recyclability may comprise at least one item of information on the presence and/or absence of recyclable compounds comprised by the material or object. Additionally or alternatively, the information on the recyclability may comprise at least one item of information on the presence and/or absence of compounds comprised by the material or object being incompatible with the recycling process, specifically with the chemical recycling process. Additionally or alternatively, the information on the recyclability may comprise at least one item of information on a level of compounds comprised by the material or object, wherein the level may be decisive if a recycling process, specifically a chemical recycling process, can be performed with the material or object.

The term "flexible foam" as used herein is a broad term and is to be given its ordinary and customary meaning to a person of ordinary skill in the art and is not to be limited to a special or customized meaning. The term specifically may refer, without limitation, to an arbitrary solidified material comprising gaseous inclusions and having elastic properties. Specifically, the flexible foam may be an elastic element, in particular such that, under a distorting force, the flexible foam may be able to distort and, when the distorting force is released, the flexible foam may be able to return to its original form. Further, the flexible foam may comprise ordered or disordered inclusions of a gaseous substance, such as air, gaseous $CO_2$ or the like. The flexible foam may specifically comprise a closed-cell foam, such as a foam having discrete gaseous inclusions which are completely surrounded by the solidified material, and/or an open-cell foam, such as a foam having interconnected gaseous inclusions. The flexible foam may be an arbitrary shaped object or item. As an example, the flexible foam may comprise a mattress. However, alternatively or additionally, the flexible foam may also comprise other foam material, such as upholstered furniture.

The term "at least partially" as used herein, specifically as used in the context of "made at least partially of", is a broad term and is to be given its ordinary and customary meaning to a person of ordinary skill in the art and is not to be limited to a special or customized meaning. The term specifically may refer, without limitation, to a situation in which an element, such as the flexible foam, is completely made of a first material and comprises no further materials and/or to a situation in which an element, such as the flexible foam, is made partially of a first material and comprises one or more further materials, such as at least one second material being different from the first material. For example, the flexible foam may be a mattress being made at least partially of at least one polyurethane. In this example, the flexible foam may comprise, besides the at least one polyurethane, further materials, specifically may comprise additives, such as flame retardants, or other filler compounds, as will be outlined in further detail below.

The term "polyurethane" as used herein is a broad term and is to be given its ordinary and customary meaning to a person of ordinary skill in the art and is not to be limited to a special or customized meaning. The term specifically may refer, without limitation, to all of the known polyisocyanate polyaddition products. These comprise adducts of isocyanate and alcohol, and they also comprise modified polyurethanes which can comprise isocyanurate structures, allophanate structures, urea structures, carbodiimide structures, uretonimine structures, and biuret structures, and which can comprise further isocyanate adducts. These polyurethanes of the invention may comprise in particular foams based on polyisocyanate polyaddition products, e.g. elastomeric foams, flexible foams, semirigid foams and rigid foams. For the purposes of the invention, the term polyurethanes may also include polymer blends comprising polyurethanes and further polymers, and also foams made of said polymer blends.

The method comprises at least the following steps which, as an example, may be performed in the given order. It shall be noted, however, that it is also possible to perform one, more than one or even all of the method steps once or repeatedly. Further, it is possible to perform two or more of the method steps simultaneously or in a timely overlapping fashion. The method may comprise further method steps which are not listed.

The method comprises:

i. at least one first determination step, comprising automatically determining, by evaluating spectral data of the flexible foam, whether at least one first chemical compound of a predetermined first list of recyclable candidate components for a first class of monomers of polyurethane is present in the flexible foam, the first list of recyclable candidate components comprising at least one first recyclable candidate component; and ii. at least one first decision step, comprising automatically deciding, on the basis of the outcome of step i., if a second determination step is required, the second determination step comprising determining whether at least one second chemical compound of a predetermined second list of recyclable candidate components for a second class of monomers of polyurethane is present in the flexible foam, specifically a second list being different from the first list, the second list of recyclable candidate components comprising at least one second recyclable candidate component.

The term "determination step" as used herein is a broad term and is to be given its ordinary and customary meaning to a person of ordinary skill in the art and is not to be limited to a special or customized meaning. The term specifically may refer, without limitation, to a process of analyzing input data in order to generate at least one quantitative and/or qualitative result. The input data of the determination step may specifically comprise the spectral data of the flexible foam. The analysis may specifically comprise a classification of the input data with respect to a presence, an absence and/or a level of a specific chemical compound in the flexible foam. The outcome of the determination step may comprise the quantitative and/or qualitative result on the input data, such as a quantitative and/or qualitative result on the presence, absence and/or level of the specific compound in the flexible foam. The process of the determination step may also be referred to as "determining".

The method, as will be outlined in further detail below, may specifically comprise a plurality of determination steps. The determination steps are numbered as "first determination step", "second determination step", "third determination step" and "fourth determination step". The numbering of the determination steps may specifically be intended to indicate an order of performance of the determination steps. Specifically, the first determination step may be performed prior to the second determination step, the second determination step may be performed prior to the third determination step and so on. However, the numbering of the determination steps may not exclude the possibility of performing the determination steps once or repeatedly. Similarly, the numbering of the determination steps may not exclude the possibility of performing further determination steps, such as a fifth determination step or the like.

As outlined above, the first determination step comprises automatically determining, by evaluating spectral data of the flexible foam, whether the at least one first chemical compound of the predetermined first list of recyclable candidate components for the first class of monomers of polyurethane is present in the flexible foam.

The term "automatically" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

The term "evaluating" as used herein is a broad term and is to be given its ordinary and customary meaning to a person of ordinary skill in the art and is not to be limited to a special or customized meaning. The term specifically may refer, without limitation, to a process of analyzing data. Specifically, as used in the context of the determination step, the evaluating may comprise analyzing the spectral data of the flexible foam. Thus, the evaluating may comprise the analysis of the spectral data of the flexible foam in the determination step in order to determine a presence, an absence and/or a level of a chemical compound in the flexible foam.

The term "spectral data" as used herein is a broad term and is to be given its ordinary and customary meaning to a person of ordinary skill in the art and is not to be limited to a special or customized meaning. The term specifically may refer, without limitation, to numerical items of information on spectral properties of at least one object. The object may specifically be the flexible foam. The spectral data may comprise at least one spectrum of the flexible foam, such as a spectrum in the optical spectral range, in particular in the infrared (IR) spectral range, especially in the near-infrared (NIR) spectral range, and/or items of information derived from the spectrum of the flexible foam. The optical spectral range may specifically refer to a partition of electromagnetic radiation comprising one or more of the visible spectral range, in particular a spectral range of 380 nm to 760 nm., the ultraviolet spectral range, in particular a spectral range of 1 nm to 380 nm, and the infrared spectral range, in particular a spectral range of 760 nm to 1000 μm, wherein the range of 760 nm to 1.5 μm is usually denominated as "near infrared spectral range" (NIR), while the range from 1.5μ to 15 μm is denoted as "mid infrared spectral range" (MidIR) and the range from 15 μm to 1000 μm as "far infrared spectral range" (FIR).

The spectrum of the flexible foam may be obtained by measuring the flexible foam using a spectrometer device, such as a handheld spectrometer device, for example being operated in reflective and/or transmissive mode. The spectrum may specifically comprise a spectral distribution of a reflectivity of the flexible foam. Alternatively or additionally, the spectrum may comprise a spectral distribution of a physical property determined by measuring a reflection of electromagnetic radiation of the flexible foam. Specifically, the spectrum may comprise a spectral distribution of an absorbance of the flexible foam, wherein the absorbance may be determined by using a reflectivity of the flexible foam, wherein the reflectivity may be determined by measuring a reflection of electromagnetic radiation of the flexible foam. The spectral data may comprise the raw spectrum of the flexible foam, such as the spectrum directly obtained by measuring the flexible foam with the spectrometer device. Alternatively or additionally, the spectral data may comprise data retrieved from the spectrum of the flexible foam, such as a first order derivative of the spectrum, a second order derivative of the spectrum, higher-order derivatives of the spectrum and/or a processed spectrum, for example a filtered and/or smoothed spectrum of the flexible foam.

The term "chemical compound" as used herein is a broad term and is to be given its ordinary and customary meaning to a person of ordinary skill in the art and is not to be limited to a special or customized meaning. The term specifically may refer, without limitation, to low molecular weight chemical compounds which may be defined by their chemical structure and their molecular weight. The term also may refer to oligomeric or polymeric chemical compounds with a defined structure or defined repeating units, which may for example be defined by an average molecular weight.

The term "first" and "second", as used in the context of the chemical compound, may refer to a specific chemical compound, as defined above, being determined in the first determination step or in the second determination step, respectively.

The term "recyclable candidate component" as used herein is a broad term and is to be given its ordinary and customary meaning to a person of ordinary skill in the art and is not to be limited to a special or customized meaning. The term specifically may refer, without limitation, to a chemical compound which can be recovered from the flexible foam in at least one predetermined recycling process. The recycling process may comprise any suitable recycling process for recovering the recyclable candidate component, such as at least one of a physical recycling process, a chemical recycling process, a mechanical recycling process and a feedstock recycling process, preferably a chemical recycling process. The recyclable candidate component may be recyclable from a complex material or object, specifically comprising a plurality of chemical compounds. For example, the recyclable candidate component may be recovered from the flexible foam, in particular from a flexible foam comprising multiple chemical compounds.

The term "first" and "second", as used in the context of the recyclable candidate component, may refer to one or more specific recyclable candidate components defining a first or second list of recyclable candidate components in the first determination step or in the second determination step, respectively.

The term "list" as used herein is a broad term and is to be given its ordinary and customary meaning to a person of ordinary skill in the art and is not to be limited to a special or customized meaning. The term specifically may refer, without limitation, to an ordered or unordered collection of data. Specifically, the list of recyclable candidate components may comprise an ordered or unordered collection of recyclable candidate components. The list of recyclable candidate components may specifically comprise, for each of the first determination step and the second determination step, a specific collection of recyclable candidate components. Thus, the list of recyclable candidate components may be referred to as the first list of recyclable candidate components for the first determination step and as the second list of recyclable candidate component for the second determination step. The second list of recyclable candidate component may be different from the first list of recyclable candidate components, in particular such that the first list of recyclable candidate components and the second list of recyclable candidate components comprise a collection of recyclable candidate components which differ in at least one recyclable candidate components from each other. The list of recyclable candidate component may comprise a single recyclable candidate component or, alternatively, a plurality of recyclable candidate components.

The lists for the first determination step and the second determination step are predetermined. The term "predetermined" as used herein is a broad term and is to be given its ordinary and customary meaning to a person of ordinary skill in the art and is not to be limited to a special or customized meaning. The term specifically may refer, without limitation, to a property of the list of being defined prior to performing the method. Specifically, the recyclable candidate components for the first list of recyclable candidate components and for the second list of recyclable candidate components may comprise predefined recyclable candidate components for the first determination step and for the second determination step, respectively.

The term "class of monomers of polyurethane" as used herein is a broad term and is to be given its ordinary and customary meaning to a person of ordinary skill in the art and is not to be limited to a special or customized meaning. The term specifically may refer, without limitation, to isocyanate monomers and compounds having at least one functional group which is capable of reacting with an isocyanate group in an addition reaction, thereby forming a chemical bond between carbon atom of the isocyanate group and one of the atoms of the functional group. These functional groups are also termed "active hydrogen functional group" or "isocyanate reactive group". Typical active hydrogen functional groups of active hydrogen compounds are the hydroxyl group (OH). Typical monomers in the context of the present invention are isocyanate monomers and polyol monomers.

The term "first" and "second", as used in the context of the class of monomers of polyurethane, may refer to a specific class of monomers of polyurethane, as defined above, defining the recyclable candidate components in the first determination step or in the second determination step, respectively.

The first class of monomers of polyurethane may comprise isocyanate monomers. The at least one isocyanate monomer may for example be selected from the group consisting of aliphatic diisocyanates, alicyclic diisocyanates and aromatic diisocyanates. The term "aliphatic diisocyanate" may refer to molecules having two isocyanate groups attached to an acyclic saturated hydrocarbon radical which typically comprises 4 to 18 carbon atoms. The term "alicyclic diisocyanate" may refer to molecules having two isocyanate groups attached to a saturated hydrocarbon radical bearing at least one cyclic moiety. Alicyclic diisocyanate may typically comprise 6 to 18 carbon atoms. The term "aromatic diisocyanate" may refer to molecules having two isocyanate groups attached directly and/or indirectly to the aromatic ring. Aromatic diisocyanates may typically have 8 to 18 carbon atoms. Examples of aromatic diisocyantes include, but are not limited to, 1,2-, 1,3-, and 1,4-phenylene diisocyanates, naphthylene-1,5-diisocyanate, 2,4- and 2,6-toluene diisocyanate, 2,4'-, 4,4'- and 2,2'-biphenyl diisocyanates, 2,2'-, 2,4'- and 4,4'-diphenylmethane diisocyanate, 1,2-, 1,3- and 1,4-xylylene diisocyanates and m-tetramethylxylyene diisocyanate (TMXDI), and mixtures thereof. Specifically, the first list of recyclable candidate components for the first class of monomers of polyurethane may comprise at least one toluene diisocyanate isomer.

The second class of monomers of polyurethane may comprise polyol monomers. Typical polyol monomers may have two or more hydroxy groups. Suitable polyol monomers may be selected from the group consisting of polyester polyols, including in particular aliphatic polyester polyols and aliphatic aromatic polyester polyols, polyestercarbonate polyols, polyetherester polyols, aliphatic polycarbonate polyols, polyacrylate polyols, polyolefine polyols, aliphatic polyetherols and mixtures thereof. Specifically, the second list of recyclable candidate components for the second class of monomers of polyurethane may comprise at least one polyol selected from the group consisting of: polyetherpolyols, polyesterpolyols. Suitable polyol monomers may for example have a number average molecular weight Mn in the range of 400 to 10,000 g/mol, preferably of 500 to 8,000 g/mol.

As outlined above, the method comprises in step ii., the at least first decision step. The term "decision step" as used herein is a broad term and is to be given its ordinary and customary meaning to a person of ordinary skill in the art and is not to be limited to a special or customized meaning. The term specifically may refer, without limitation, to a process of selecting one option out of a plurality of options. The decision step may specifically comprise selecting one option selected from the group consisting of: a further determination step is required; no further determination step is required. In case the decision step selects the option that a further determination is required, the method may advance with performing a subsequent determination step. Alternatively, in case the decision step selects the option that no further determination is required, the method may comprise outputting an item of information indicating that the flexible foam is not recyclable. Decisive for the decision made in the decision step may be the outcome of the preceding determination step. For example, if the preceding determination step determines that a specific recyclable candidate component is present in the flexible foam, the decision step may comprise selecting the option that a further determination step is required. Thus, in this case, the method may advance in performing a further determination step. As another example, if the preceding determination step determines that a specific recyclable candidate component is not present in the flexible foam, the decision step may comprise selecting the option that no further determination step is required. In this case, the method may comprise outputting an item of information indicating that the flexible foam is not recyclable. Further, in contrast to preceding decision steps, a last decision step of the method, for example a fourth determination step, as will be outlined in further detail below, may comprise selecting one option selected from the group consisting of: flexible foam is recyclable; flexible foam is not recyclable. The process of the decision step may also be referred to as "deciding".

The method, as will be outlined in further detail below, may specifically comprise a plurality of decision steps. The decision steps are numbered as "first decision step", "second decision step" and "third decision step". The numbering of the decision steps may specifically be intended to indicate an order of performance of the decision steps. Specifically, the first decision step may be performed prior to the second decision step and the second decision step may be performed prior to the third decision step. However, the numbering of the decision steps may not exclude the possibility of performing the decision steps once or repeatedly. Similarly, the numbering of the decision steps may not exclude the possibility of performing further decision steps, such as a fourth decision step or the like.

Step i., specifically the first determination step, may comprise comparing the spectral data of the flexible foam with at least one first reference spectrum of at least one first flexible reference foam made at least partially of at least one polyurethane comprising the at least one first chemical compound of the first list of recyclable candidate components. The term "reference spectrum" as used herein is a broad term and is to be given its ordinary and customary meaning to a person of ordinary skill in the art and is not to be limited to a special or customized meaning. The term specifically may refer, without limitation, to spectral data of a reference object. The reference object may specifically be a flexible reference foam. The reference spectrum may comprise a raw spectrum of the flexible reference foam, such as the spectrum directly obtained by measuring the flexible reference foam with the spectrometer device. Alternatively or additionally, the reference spectrum may comprise data retrieved from the raw spectrum of the flexible reference foam, such as a first order derivative of the raw spectrum, a second order derivative of the raw spectrum, higher-order derivatives of the raw spectrum and/or a processed spectrum, for example a filtered and/or smoothed spectrum of the flexible reference foam.

The method, as will be outlined in further detail below, may specifically comprise using a plurality of reference spectra. The reference spectra are numbered as "first reference spectrum", "second reference spectrum", "third reference spectrum" and "fourth reference spectrum", wherein the numbering is intended to indicate the determination step in which the respective reference spectrum may be used. Thus, the first reference spectrum may be used in the first determination step, the second reference spectrum may be used in the second determination step and so on.

The term "flexible reference foam" as used herein is a broad term and is to be given its ordinary and customary meaning to a person of ordinary skill in the art and is not to be limited to a special or customized meaning. The term specifically may refer, without limitation, to a flexible foam of fully or partially known composition. Specifically, the flexible reference foam may have a known composition of its chemical compounds and, thus, may be suitable for being used as a reference object. The first flexible reference foam may be used for obtaining the first reference spectrum. Similarly, a second flexible reference foam may be used for obtaining a second reference spectrum, a third flexible reference foam may be used for obtaining a third reference spectrum and a fourth flexible reference foam may be used for obtaining a fourth reference spectrum, as will be outlined in further detail below.

Step i., specifically the first determination step, may comprise applying at least one first trained model to the spectral data. The term "trained model" as used herein is a broad term and is to be given its ordinary and customary meaning to a person of ordinary skill in the art and is not to be limited to a special or customized meaning. The term specifically may refer, without limitation, to a mathematical model for data interpretation, e.g. data classification, wherein the trained model is trainable on at least one training dataset. In the trained model, one or more parameters may still be variable, and the setting of the parameters is up to a training process. The trained model may provide for a model of an environment, and the model may be adapted for reacting to stimuli from the environment in an adequate fashion and for adjusting the model in accordance with observed deviations such that, in a subsequent run, the model reacts to stimuli in a more adequate fashion. The trained model may be trained on at least one training data set and may be configured for predicting at least one target variable for at least one input variable, such that, as an example, the at least one input variable forms a stimulus, and the output target variable forms the response of the trained model. A plurality of trainable models is generally known to the skilled person in the field of artificial intelligence and machine learning. However, for the purpose indicated herein, various trained models may be favorable. Thus, specifically, the trained model may comprise at least one trained model selected from the group consisting of: a principle component analysis model; a regression model, specifically a partial least square regression model; a principle component regression model; a lasso regression model;

a nearest neighbor model; an artificial neural network, specifically an artificial neural network selected from the group consisting of a deep neural network, a convolutional neural network, a recurrent neural network, a long-short-term neural network; a support vector machine model; a decision tree classifier model; a decision tree classificatory, specifically at least one of a Random Forest Classifier and a Boosted Decision Tree Classifier. It shall be noted that combinations of trained models are also feasible, such as combinations comprising at least one trained model selected from the list as indicated above. Further, hybrid models are also feasible.

The method, as will be outlined in further detail below, may specifically comprise applying a plurality of trained models. The trained models are numbered as "first trained model", "second trained model", "third trained model" and "fourth trained model", wherein the numbering is intended to indicate the determination step in which the respective trained model may be applied. Thus, the first trained model be applied in the first determination step, the second trained model may be applied in the second determination step and so on. However, the numbering may not necessarily indicate different trained models. Specifically, two or more or even all of the applied trained models may comprise the same trained model or, alternatively, different trained models.

The first trained model may be capable of discriminating between spectral data of flexible foams made at least partially of at least one polyurethane comprising the at least one first chemical compound of the first list of recyclable candidate components and spectral data of flexible foams made at least partially of at least one polyurethane, not comprising the at least one first chemical compound of the first list of recyclable candidate components.

The trained model may be trained by using at least one set of spectral training data. The term "spectral training data" as used herein is a broad term and is to be given its ordinary and customary meaning to a person of ordinary skill in the art and is not to be limited to a special or customized meaning. The term specifically may refer, without limitation, to spectral data used or usable for training the trained model. The spectral training data may be known or predetermined. Specifically, the spectral training data may be or may comprise historical experimental data such as previously experimentally determined data. Additionally or alternatively, the spectral training data may comprise theoretical data such as theoretically calculated data, specifically simulated data. The spectral training data may be numbered according to their use for training the respective trained model.

The first trained model may be trained by using at least one first set of spectral training data. The at least one first set of spectral training data may comprise spectral training data of at least one flexible foam made at least partially of at least one polyurethane comprising the at least one first chemical compound of the first list of recyclable candidate components and spectral training data of at least one flexible foam made at least partially of at least one polyurethane not comprising the at least one first chemical compound of the first list of recyclable candidate components.

The method may further comprise, if it is determined in the first determination step that the first chemical compound of the first list of recyclable candidate components is not present in the flexible foam, generating at least one item of information indicating that the flexible foam is not recyclable. Alternatively, if it is determined that the first chemical compound of the first list of recyclable candidate components is present in the flexible foam, the method may further comprise the following step:

iii. performing the second determination step.

Step iii. may comprise comparing the spectral data of the flexible foam with at least one second reference spectrum of at least one second flexible reference foam made at least partially of at least one polyurethane comprising the at least one second chemical compound of the second list of recyclable candidate components.

Alternatively or additionally, step iii. may comprise applying at least one second trained model to the spectral data. The second trained model may be different or identical to the first trained model. The second trained model may be capable of discriminating between spectral data of flexible foams made at least partially of at least one polyurethane comprising the at least one second chemical compound of the second list of recyclable candidate components and spectral data of flexible foams made at least partially of at least one polyurethane not comprising the at least one second chemical compound of the second list of recyclable candidate components.

In particular, the determination of the second chemical compound may comprise using a lower accuracy compared with the determination of the first chemical compound. The accuracy, as an example, may be determined by experiments, e.g. by dividing the sum of the correct classifications by using the respective trained model by the sum of the experiments or data sets in total. A higher accuracy, however, is often achieved by a higher effort of calculation or higher use of resources. So the method as prosed herein may comprise a decrease in accuracy from determination step to determination step, in order to reduce calculation time and effort. More specifically, a ranking can be implied, wherein the importance of the classes of monomers decreases from determination step to determination step, in accordance with a predetermined ranking, e.g. according to the value of the recoverable chemical components. Thus, the accuracy of the optional second determination step may be lower than the accuracy of the first determination step, the accuracy of the optional third determination step may be lower than the accuracy of the optional second determination step, and the accuracy of the optional fourth determination step may be lower than the accuracy of the optional third determination step. Thereby, the effort of calculation may be reduced in accordance with a predetermined ranking of the classes of monomers, e.g. by decreasing the value of the classes of monomers from determination step to determination step and by reducing the accuracy of the determination step from determination step to determination step.

The second trained model may be trained by using at least one second set of spectral training data. The at least one second set of spectral training data may comprise spectral training data of at least one flexible foam made at least partially of at least one polyurethane comprising the at least one second chemical compound of the second list of recyclable candidate components and spectral training data of at least one flexible foam made at least partially of at least one polyurethane not comprising the at least one second chemical compound of the second list of recyclable candidate components.

The method may further comprise:

iv. at least one second decision step, comprising automatically deciding, after performing step iii., on the basis of the outcome of step iii., if a third determination step is required, the third determination step comprising determining whether at least one flame retardant compound of a predetermined third list of candidate flame retardant components is present in the flexible foam, the third list of candidate flame retardant components comprising at least one flame retardant candidate component.

The term "flame retardant" as used herein is a broad term and is to be given its ordinary and customary meaning to a person of ordinary skill in the art and is not to be limited to a special or customized meaning. The term specifically may refer, without limitation, to a chemical compound configured for inhibiting ignition of an object. Specifically, the flame retardant may comprise a chemical compound configured for inhibiting ignition of the flexible foam, such as of a mattress or any other foam material, such as upholstered furniture.

The method may further comprise, if it is determined in the second decision step that the second chemical compound of the second list of recyclable candidate components is not present in the flexible foam, generating at least one item of information indicating that the flexible foam is not recyclable. Alternatively, if it is determined that the second chemical compound of the second list of recyclable candidate components is present in the flexible foam, the method may further comprise the following step:

v. performing the third determination step.

The third list of candidate flame retardant components may comprise at least one flame retardant component selected from the group consisting of: melamine derivatives, phosphates, derivatives of phosphoric acid, derivatives of phosphonic acid and derivatives of phosphinic acid.

Step v. may specifically comprise comparing the spectral data of the flexible foam with at least one third reference spectrum of at least one third flexible reference foam comprising at least one candidate flame retardant component of the third list of candidate flame retardant components.

Alternatively or additionally, step v. may comprise applying at least one third trained model to the spectral data. The third trained model may be different or identical to the first trained model and/or the second trained model. The third trained model may be capable of discriminating between spectral data of flexible foams comprising the at least one candidate flame retardant component of the third list of candidate flame retardant components and spectral data of flexible foams not comprising the at least one candidate flame retardant component of the third list of candidate flame retardant components. In particular, the determination of the flame retardant compound may comprise using a lower accuracy compared with the determination of the first chemical compound and/or the second chemical compound, as discussed above.

The third trained model may be trained by using at least one third set of spectral training data. The at least one third set of spectral training data may comprise spectral training data of at least one flexible foam made at least partially of at least one polyurethane comprising the at least one candidate flame retardant component of the third list of candidate flame retardant components and spectral training data of at least one flexible foam made at least partially of at least one polyurethane not comprising the at least one candidate flame retardant component of the third list of candidate flame retardant components.

The method may further comprise:

vi. at least one third decision step, comprising automatically deciding, after performing step v., on the basis of the outcome of step v., if a fourth determination step is required, the fourth determination step comprising determining the content of at least one filler compound of a predetermined fourth list of candidate filler compounds in the flexible foam, the fourth list of candidate filler compounds comprising at least one candidate filler compound.

The term "filler compound" as used herein is a broad term and is to be given its ordinary and customary meaning to a person of ordinary skill in the art and is not to be limited to a special or customized meaning. The term specifically may refer, without limitation, to organic or inorganic filler materials such as for example mineral fillers or polymers. Suitable polymers may for example be polymers prepared using one or more olefinic monomers such as acrylonitrile, styrene, (meth)acrylates, (meth)acrylic acid and/or acrylamide.

The method may comprise, if it is determined in the third decision step that the at least one flame retardant compound of the third list of candidate flame retardant components is not present in the flexible foam, generating at least one item of information indicating that the flexible foam is not recyclable. Alternatively, if it is determined that the at least one flame retardant compound of the third list of candidate flame retardant components is present in the flexible foam, the method may further comprise the following step:

vii. performing the fourth determination step.

The fourth list of candidate filler compounds may comprise at least one filler compound selected from the group consisting of: polymers prepared using one or more olefinic monomers such as acrylonitrile, styrene, (meth)acrylates, (meth)acrylic acid and/or acrylamide.

Step vii. may specifically comprise comparing the spectral data of the flexible foam with at least one fourth reference spectrum of at least one fourth flexible reference foam comprising at least one candidate filler compound of the fourth list of candidate filler compounds.

Additionally or alternatively, step vii. may comprise applying at least one fourth trained model to the spectral data. The fourth trained model may be different or identical to the first trained model, the second trained model and/or the third trained model. The fourth trained model may be capable of discriminating between spectral data of flexible foams comprising the at least one candidate filler compound of the fourth list of candidate filler compounds and spectral data of flexible foams not comprising the at least one candidate filler compound of the fourth list of candidate filler compounds. In particular, the determination of the filler compound may comprise using a lower accuracy compared with the determination of the first chemical compound, the second chemical compound and/or the flame retardant compound, as discussed above.

The fourth trained model may be trained by using at least one fourth set of spectral training data. The at least one fourth set of spectral training data may comprise spectral training data of at least one flexible foam made at least partially of at least one polyurethane comprising the at least one candidate filler compound of the fourth list of candidate filler compounds and spectral training data of at least one flexible foam made at least partially of at least one polyurethane not comprising the at least one candidate filler compound of the fourth list of candidate filler compounds.

The content of the at least one filler compound may be compared with at least tolerance level, wherein, if the content exceeds the tolerance level, the method may comprise generating at least one item of information indicating that the flexible foam is not recyclable; and if the content does not exceed the tolerance level, the method may comprise generating at least one item of information indicating that the flexible foam is recyclable.

In a further aspect of the present invention, a computer program is disclosed, comprising instructions which, when the instructions are executed by at least one processor, cause the processor to perform the method of obtaining information on the recyclability of at least one flexible foam made at least partially of at least one polyurethane according to the present invention, such as according to any one of the embodiments disclosed above and/or according to any one of the embodiments disclosed in further detail below.

In a further aspect of the present invention, a computer-readable storage medium, specifically a non-transient computer-readable storage medium, is disclosed, comprising instructions which, when the instructions are executed by at least one processor, cause the processor to perform the method of obtaining information on the recyclability of at least one flexible foam made at least partially of at least one polyurethane according to the present invention, such as according to any one of the embodiments disclosed above and/or according to any one of the embodiments disclosed in further detail below.

As used herein, the term "computer-readable storage medium" specifically may refer to non-transitory data storage means, such as a hardware storage medium having stored thereon computer-executable instructions. The computer-readable storage medium specifically may be or may comprise a storage medium such as a random-access memory (RAM) and/or a read-only memory (ROM).

In a further aspect of the present invention, a method of treatment of at least one flexible foam made at least partially of at least one polyurethane is disclosed. For definitions and possible embodiments of the method, reference may be made to definitions and embodiments of the method of obtaining information on the recyclability of at least one flexible foam made at least partially of at least one polyurethane, as outlined in further detail above.

The method comprises at least the following steps which, as an example, may be performed in the given order. It shall be noted, however, that a different order is also possible. Further, it is also possible to perform one, more than one or even all of the method steps once or repeatedly. Further, it is possible to perform two or more of the method steps simultaneously or in a timely overlapping fashion. The method may comprise further method steps which are not listed.

The method comprises:

I. obtaining spectral data of the flexible foam, specifically in the near infrared spectral range;

II. obtaining information on the recyclability of the flexible foam by using the by using the spectral data and by using the method of obtaining information on the recyclability of at least one flexible foam made at least partially of at least one polyurethane according to the present invention, such as according to any one of the embodiments disclosed above and/or according to any one of the embodiments disclosed in further detail below; and III. determining, on the basis of the information gained in step III., whether or not to recycle the flexible foam and, if the information indicates a recyclability of the flexible foam, at least partially recycling the flexible foam.

In a further aspect of the present invention, a device for obtaining information on the recyclability of at least one flexible foam made at least partially of at least one polyurethane is disclosed. For definitions and possible embodiments of the device, reference may be made to definitions and embodiments of the method of obtaining information on the recyclability of at least one flexible foam made at least partially of at least one polyurethane, as outlined in further detail above.

The device comprises at least one processor. The term "processor" as used herein is a broad term and is to be given its ordinary and customary meaning to a person of ordinary skill in the art and is not to be limited to a special or customized meaning. The term specifically may refer, without limitation, to an arbitrary logic circuitry configured for performing basic operations of a computer or system, and/or, generally, to a device which is configured for performing calculations or logic operations. In particular, the processor may be configured for processing basic instructions that drive the computer or system. As an example, the processor may comprise at least one arithmetic logic unit (ALU), at least one floating-point unit (FPU), such as a math coprocessor or a numeric co-processor, a plurality of registers, specifically registers configured for supplying operands to the ALU and storing results of operations, and a memory, such as an L1 and L2 cache memory. In particular, the processor may be a multi-core processor. Specifically, the processor may be or may comprise a central processing unit (CPU). Additionally or alternatively, the processor may be or may comprise a microprocessor, thus specifically the processor's elements may be contained in one single integrated circuitry (IC) chip. Additionally or alternatively, the processor may be or may comprise one or more application-specific integrated circuits (ASICs) and/or one or more field-programmable gate arrays (FPGAs) and/or one or more tensor processing unit (TPU) and/or one or more chip, such as a dedicated machine learning optimized chip, or the like.

The processor is configured, specifically by software programming, for performing the method of obtaining information on the recyclability of at least one flexible foam made at least partially of at least one polyurethane according to the present invention, such as according to any one of the embodiments disclosed above and/or according to any one of the embodiments disclosed in further detail below.

In a further aspect of the present invention, a system for treatment of at least one flexible foam made at least partially of at least one polyurethane is disclosed.

The term "system" as used herein is a broad term and is to be given its ordinary and customary meaning to a person of ordinary skill in the art and is not to be limited to a special or customized meaning. The term specifically may refer, without limitation, to an arbitrary set of interacting or interdependent components parts forming a whole. Specifically, the components may interact with each other in order to fulfill at least one common function. The system may comprise at least two components which may be handled independently from each other or may be coupled or connectable.

The system comprises:

A. at least one retrieving device for retrieving spectral data of the flexible foam, specifically in the near infrared spectral range, specifically at least one spectrometer device;

B. at least one device according to the preceding claim; and

C. at least one recycling system for at least partially recycling the flexible foam.

The term "retrieving device" as used herein is a broad term and is to be given its ordinary and customary meaning to a person of ordinary skill in the art and is not to be limited to a special or customized meaning. The term specifically may refer, without limitation, to an interface device configured for interacting with at least one other device and/or at least one object. Specifically, the retrieving device may comprise a spectrometer device configure for optically interacting with at least one object, such as the at least one flexible foam, thereby generating the spectral data. Alternatively or additionally, the retrieving device may comprise a data storage unit, such as a working memory or a main memory of a computer or computer network, wherein the data storage unit may be configured for storing the spectral data. Alternatively or additionally, the retrieving device may comprise at least one interface for receiving the spectral data from at least one other device and/or for reading the spectral data from a data storage unit. The interface may specifically be configured for providing the received spectral data to further devices, such as to the device for obtaining information on the recyclability of the flexible foam.

The term "recycling system" as used herein is a broad term and is to be given its ordinary and customary meaning to a person of ordinary skill in the art and is not to be limited to a special or customized meaning. The term specifically may refer, without limitation, to an arbitrary system configured for performing at least one recycling process, specifically at least one physical recycling process, chemical recycling process, mechanical recycling process and/or feedstock recycling process. Preferably, the recycling system may be configured for performing at least one chemical recycling process, specifically a chemical recycling process for recycling polyurethane.

The methods and devices according to the present invention may provide a large number of advantages over known methods and systems. Specifically, the methods and devices according to the present invention may allow for obtaining information on the recyclability of at least one flexible foam made at least partially of at least one polyurethane and, thus, to enable an accurate and reliable sorting of flexible foams comprising polyurethane prior to the chemical recycling process. As an example, the chemical compounds of polyurethane mattresses may be identified using spectral data, such as spectral data obtained by near-infrared spectroscopy using a handheld spectrometer device. The handheld spectrometer device may be used on the spot and, thus, recyclable flexible foams can be identified on the spot in short time. This procedure may specifically reduce costs and enhance throughput compared with known methods and device, specifically compared to lab analysis of the flexible foam's components. A user of the handheld spectrometer device may cut open the flexible foam, such as the mattress ticking, and may measure the flexible foam with the handheld spectrometer device. The obtained spectral data, such as the spectrum of the flexible foam, may be automatically analyzed by the at least one trained model, which specifically was trained on the at least one set of spectral training data comprising spectral training data of flexible foams with known composition. The spectral data of the flexible foam may be analyzed in a step-wise analysis, specifically comprising one or more determination steps and one or more decision steps, and, as a result, may be classified as recyclable or not recyclable.

As used herein, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically are used only once when introducing the respective feature or element. In most cases, when referring to the respective feature or element, the expressions "at least one" or "one or more" are not repeated, notwithstanding the fact that the respective feature or element may be present once or more than once.

Further, as used herein, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

Summarizing and without excluding further possible embodiments, the following embodiments may be envisaged:

Embodiment 1: A computer-implemented method of obtaining information on the recyclability of at least one flexible foam made at least partially of at least one polyurethane, the method comprising:

i. at least one first determination step, comprising automatically determining, by evaluating spectral data of the flexible foam, whether at least one first chemical compound of a predetermined first list of recyclable candidate components for a first class of monomers of polyurethane is present in the flexible foam, the first list of recyclable candidate components comprising at least one first recyclable candidate component; and ii. at least one first decision step, comprising automatically deciding, on the basis of the outcome of step i., if a second determination step is required, the second determination step comprising determining whether at least one second chemical compound of a predetermined second list of recyclable candidate components for a second class of monomers of polyurethane is present in the flexible foam, specifically a second list being different from the first list, the second list of recyclable candidate components comprising at least one second recyclable candidate component.

Embodiment 2: The method according to the preceding embodiment, wherein the first class of monomers of polyurethane comprises isocyanate monomers.

Embodiment 3: The method according to the preceding embodiment, wherein the first list of recyclable candidate components for the first class of monomers of polyurethane comprises at least one toluene diisocyanate isomer.

Embodiment 4: The method according to any one of the preceding embodiments, wherein step i. comprises comparing the spectral data of the flexible foam with at least one first reference spectrum of at least one first flexible reference foam made at least partially of at least one polyurethane comprising the at least one first chemical compound of the first list of recyclable candidate components.

Embodiment 5: The method according to any one of the preceding embodiments, wherein step i. comprises applying at least one first trained model to the spectral data, the first trained model being capable of discriminating between spectral data of flexible foams made at least partially of at least one polyurethane comprising the at least one first chemical compound of the first list of recyclable candidate components and spectral data of flexible foams made at least partially of at least one polyurethane, not comprising the at least one first chemical compound of the first list of recyclable candidate components.

Embodiment 6: The method according to the preceding embodiment, wherein the first trained model is trained by using at least one first set of spectral training data, the at least one first set of spectral training data comprising spectral training data of at least one flexible foam made at least partially of at least one polyurethane comprising the at least one first chemical compound of the first list of recyclable candidate components and spectral training data of at least one flexible foam made at least partially of at least one polyurethane not comprising the at least one first chemical compound of the first list of recyclable candidate components.

Embodiment 7: The method according to any one of the preceding embodiments, wherein, if it is determined in the first determination step that the first chemical compound of the first list of recyclable candidate components is not present in the flexible foam, the method comprises generating at least one item of information indicating that the flexible foam is not recyclable, or else, if it is determined that the first chemical compound of the first list of recyclable candidate components is present in the flexible foam, the method further comprises the following step:

iii. performing the second determination step.

Embodiment 8: The method according to the preceding embodiment, wherein the second class of monomers of polyurethane comprises polyol monomers.

Embodiment 9: The method according to the preceding embodiment, wherein the second list of recyclable candidate components for the second class of monomers of polyurethane comprises at least one polyol selected from the group consisting of: polyetherpolyols, polyesterpolyols.

Embodiment 10: The method according to any one of the three preceding embodiments, wherein step iii. comprises comparing the spectral data of the flexible foam with at least one second reference spectrum of at least one second flexible reference foam made at least partially of at least one polyurethane comprising the at least one second chemical compound of the second list of recyclable candidate components.

Embodiment 11: The method according to any one of the four preceding embodiments, wherein step iii. comprises applying at least one second trained model to the spectral data, the second trained model being capable of discriminating between spectral data of flexible foams made at least partially of at least one polyurethane comprising the at least one second chemical compound of the second list of recyclable candidate components and spectral data of flexible foams made at least partially of at least one polyurethane not comprising the at least one second chemical compound of the second list of recyclable candidate components.

Embodiment 12: The method according to the preceding embodiment, wherein the second trained model is trained by using at least one second set of spectral training data, the at least one second set of spectral training data comprising spectral training data of at least one flexible foam made at least partially of at least one polyurethane comprising the at least one second chemical compound of the second list of recyclable candidate components and spectral training data of at least one flexible foam made at least partially of at least one polyurethane not comprising the at least one second chemical compound of the second list of recyclable candidate components.

Embodiment 13: The method according to any one of the six preceding embodiments, further comprising:

iv. at least one second decision step, comprising automatically deciding, after performing step iii., on the basis of the outcome of step iii., if a third determination step is required, the third determination step comprising determining whether at least one flame retardant compound of a predetermined third list of candidate flame retardant components is present in the flexible foam, the third list of candidate flame retardant components comprising at least one flame retardant candidate component.

Embodiment 14: The method according to the preceding embodiment, wherein, if it is determined in the second decision step that the second chemical compound of the second list of recyclable candidate components is not present in the flexible foam, the method comprises generating at least one item of information indicating that the flexible foam is not recyclable, or else, if it is determined that the second chemical compound of the second list of recyclable candidate components is present in the flexible foam, the method further comprises the following step:

v. performing the third determination step.

Embodiment 15: The method according to the preceding embodiment, wherein the third list of candidate flame retardant components comprises at least one flame retardant component selected from the group consisting of: melamine derivatives, phosphates, derivatives of phosphoric acid, derivatives of phosphonic acid and derivatives of phosphinic acid.

Embodiment 16: The method according to any one of the two preceding embodiments, wherein step v. comprises comparing the spectral data of the flexible foam with at least one third reference spectrum of at least one third flexible reference foam comprising at least one candidate flame retardant component of the third list of candidate flame retardant components.

Embodiment 17: The method according to any one of the three preceding embodiments, wherein step v. comprises applying at least one third trained model to the spectral data, the third trained model being capable of discriminating between spectral data of flexible foams comprising the at least one candidate flame retardant component of the third list of candidate flame retardant components and spectral data of flexible foams not comprising the at least one candidate flame retardant component of the third list of candidate flame retardant components.

Embodiment 18: The method according to the preceding embodiment, wherein the third trained model is trained by using at least one third set of spectral training data, the at least one third set of spectral training data comprising spectral training data of at least one flexible foam made at least partially of at least one polyurethane comprising the at least one candidate flame retardant component of the third list of candidate flame retardant components and spectral training data of at least one flexible foam made at least partially of at least one polyurethane not comprising the at least one candidate flame retardant component of the third list of candidate flame retardant components.

Embodiment 19: The method according to any one of the five preceding embodiments, further comprising:

vi. at least one third decision step, comprising automatically deciding, after performing step v., on the basis of the outcome of step v., if a fourth determination step is required, the fourth determination step comprising determining the content of at least one filler compound of a predetermined fourth list of candidate filler compounds in the flexible foam, the fourth list of candidate filler compounds comprising at least one candidate filler compound.

Embodiment 20: The method according to the preceding embodiment, wherein, if it is determined in the third decision step that the at least one flame retardant compound of the third list of candidate flame retardant components is not present in the flexible foam, the method comprises generating at least one item of information indicating that the flexible foam is not recyclable, or else, if it is determined that the at least one flame retardant compound of the third list of candidate flame retardant components is present in the flexible foam, the method further comprises the following step:

vii. performing the fourth determination step.

Embodiment 21: The method according to the preceding embodiment, wherein the fourth list of candidate filler compounds comprises at least one filler compound selected from the group consisting of: polymers prepared using one or more olefinic monomers such as acrylonitrile, styrene, (meth)acrylates, (meth)acrylic acid and/or acrylamide.

Embodiment 22: The method according to any one of the two preceding embodiments, wherein step vii. comprises comparing the spectral data of the flexible foam with at least one fourth reference spectrum of at least one fourth flexible reference foam comprising at least one candidate filler compound of the fourth list of candidate filler compounds.

Embodiment 23: The method according to any one of the three preceding embodiments, wherein step vii. comprises applying at least one fourth trained model to the spectral data, the fourth trained model being capable of discriminating between spectral data of flexible foams comprising the at least one candidate filler compound of the fourth list of candidate filler compounds and spectral data of flexible foams not comprising the at least one candidate filler compound of the fourth list of candidate filler compounds.

Embodiment 24: The method according to the preceding embodiment, wherein the fourth trained model is trained by using at least one fourth set of spectral training data, the at least one fourth set of spectral training data comprising spectral training data of at least one flexible foam made at least partially of at least one polyurethane comprising the at least one candidate filler compound of the fourth list of candidate filler compounds and spectral training data of at least one flexible foam made at least partially of at least one polyurethane not comprising the at least one candidate filler compound of the fourth list of candidate filler compounds.

Embodiment 25: The method according to any one of the five preceding embodiments, wherein the content of the at least one filler compound is compared with at least tolerance level, wherein, if the content exceeds the tolerance level, the method comprises generating at least one item of information indicating that the flexible foam is not recyclable; and if the content does not exceed the tolerance level, the method comprises generating at least one item of information indicating that the flexible foam is recyclable.

Embodiment 26: A computer program comprising instructions which, when the instructions are executed by at least one processor, cause the processor to perform the method according to any one of the preceding embodiments.

Embodiment 27: A computer-readable storage medium, specifically a non-transient computer-readable storage medium, comprising instructions which, when the instructions are executed by at least one processor, cause the processor to perform the method according to any one of the preceding embodiments referring to a method.

Embodiment 28: A method of treatment of at least one flexible foam made at least partially of at least one polyurethane, the method comprising:

I. obtaining spectral data of the flexible foam, specifically in the near infrared spectral range;

II. obtaining information on the recyclability of the flexible foam by using the by using the spectral data and by using the method according to any one of the preceding embodiments referring to a method on the spectral data; and III. determining, on the basis of the information gained in step III., whether or not to recycle the flexible foam and, if the information indicates a recyclability of the flexible foam, at least partially recycling the flexible foam.

Embodiment 29: A device for obtaining information on the recyclability of at least one flexible foam made at least partially of at least one polyurethane, the device comprising at least one processor, the processor being configured, specifically by software programming, for performing the method according to any one of the preceding embodiments referring to a method of obtaining information on the recyclability of at least one flexible foam made at least partially of at least one polyurethane.

Embodiment 30: A system for treatment of at least one flexible foam made at least partially of at least one polyurethane, the system comprising:

A. at least one retrieving device for retrieving spectral data of the flexible foam, specifically in the near infrared spectral range, specifically at least one spectrometer device;

B. at least one device according to the preceding embodiment; and

C. at least one recycling system for at least partially recycling the flexible foam.

SHORT DESCRIPTION OF THE FIGURES

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

DETAILED DESCRIPTION OF THE EMBODIMENTS

Figure 1:
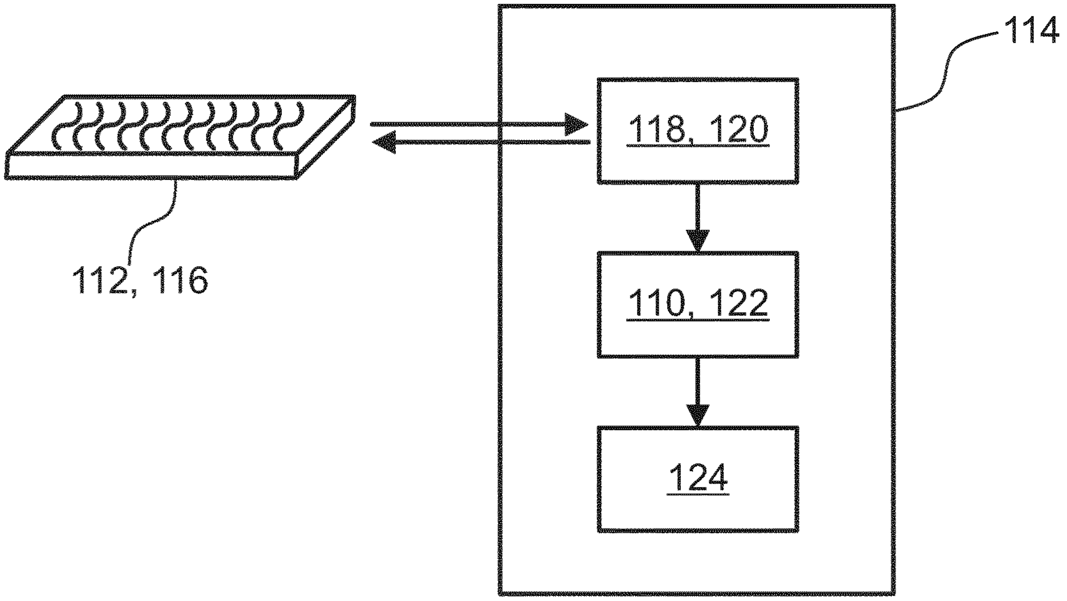
FIG. 1 shows embodiments of a device for obtaining information on the recyclability of at least one flexible foam made at least partially of at least one polyurethane and of a system for treatment of at least one flexible foam made at least partially of at least one polyurethane in a schematic view.

FIG. 1 shows exemplary embodiments of a device 110 for obtaining information on the recyclability of at least one flexible foam 112 made at least partially of at least one polyurethane and of a system 114 for treatment of the at least one flexible foam 112 made at least partially of the at least one polyurethane in a schematic view. In the example of FIG. 1, the flexible foam 112 may comprise at least one mattress 116. However, the flexible foam 112 may also comprise other foam material, such as upholstered furniture or the like.

The system 114 comprises at least one retrieving device 118 for retrieving spectral data of the flexible foam 112. The retrieving device 118 may specifically comprise at least one spectrometer device 120, in particular for retrieving spectral data in the near infrared spectral range. Thus, as schematically shown in FIG. 1, the retrieving device 118 may be configured for optically interacting with the flexible foam 112 for generating the spectral data.

The system 114 further comprises the device 110 for obtaining information on the recyclability of the flexible foam 112 made at least partially of the at least one polyurethane. The retrieving device 118 and the device 110 may be configured for interacting with each other, specifically for exchanging data or information with each other. Thus, the retrieving device 118 may be configured for providing the retrieved spectral data to the device 110. The retrieving device 118 and the device 110 may fully or partially be separate from each other or, alternatively, may also be fully or partially be integrated into one another. The device 110 may also be fully or partially be embodied as a cloud device.

The device 110 may comprise at least one processor 122. The processor 122 is configured, specifically by software programming, for performing a method of obtaining information on the recyclability of the flexible foam 112 made at least partially of the at least one polyurethane according to the present invention, such as according to the exemplary embodiment shown in FIG. 2. Thus, for a description of the method, reference may be made to the description of FIG. 2. However, the processor 122 may also be configured for performing the method in any other embodiment disclosed herein.

The system 114 further comprises at least one recycling system 124 for at least partially recycling the flexible foam 112. The device 110 and the recycling system 124 may be configured for interacting with each other, specifically for exchanging data or information with each other. Thus, the device 110 may be configured for providing the information on the recyclability of the flexible foam 112 to the recycling system 124. The recycling system 124 may be configured for performing at least one recycling process, specifically a chemical recycling process, according the information on the recyclability of the flexible foam 112.

Figure 2:
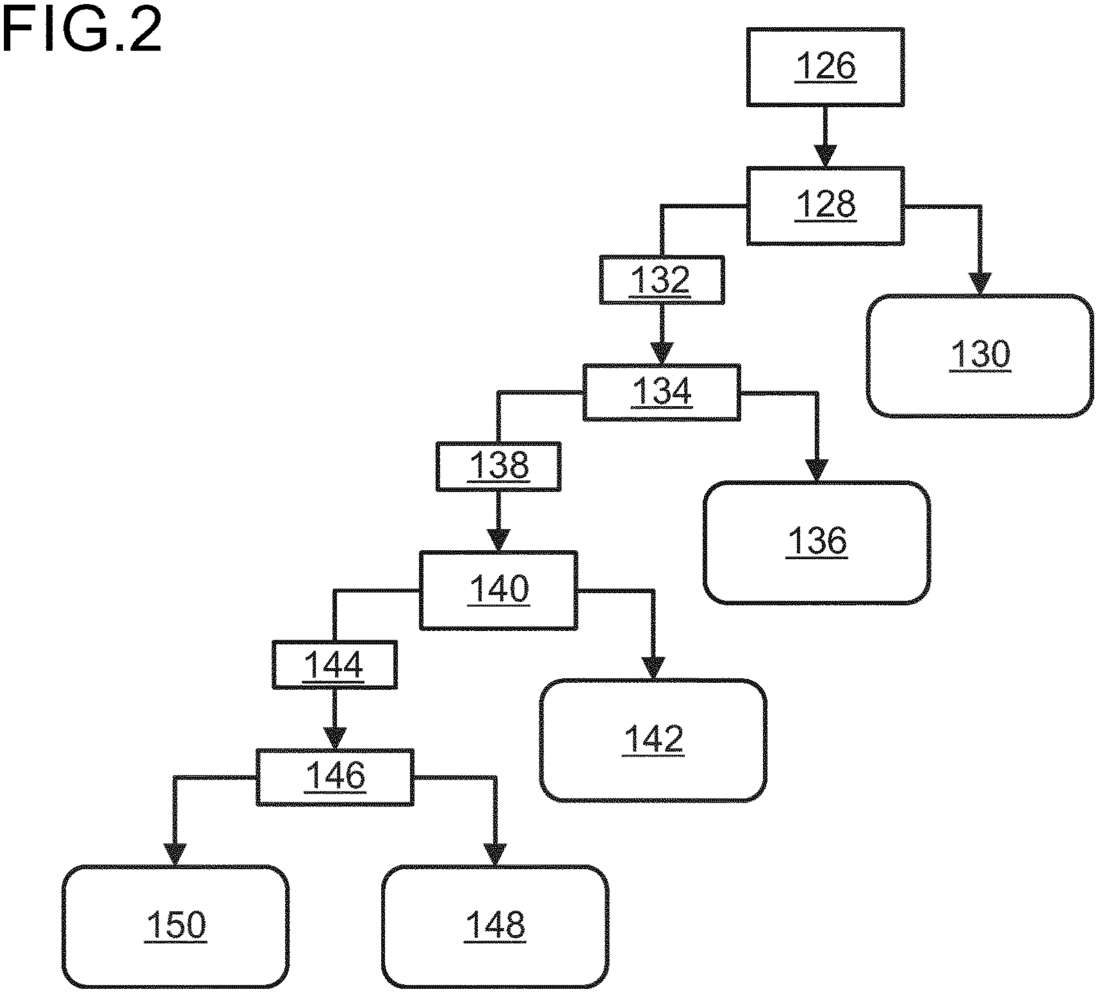
FIG. 2 shows a flow chart of an embodiment of a computer-implemented method of obtaining information on the recyclability of at least one flexible foam made at least partially of at least one polyurethane.

FIG. 2 shows a flow chart of an exemplary embodiment of a computer-implemented method of obtaining information on the recyclability of the flexible foam 112 made at least partially of the at least one polyurethane. The method comprises:

- i. (denoted by reference number 126) at least one first determination step, comprising automatically determining, by evaluating spectral data of the flexible foam 112, whether at least one first chemical compound of a predetermined first list of recyclable candidate components for a first class of monomers of polyurethane is present in the flexible foam 112, the first list of recyclable candidate components comprising at least one first recyclable candidate component; and
- ii. (denoted by reference number 128) at least one first decision step, comprising automatically deciding, on the basis of the outcome of step i., if a second determination step is required, the second determination step comprising determining whether at least one second chemical compound of a predetermined second list of recyclable candidate components for a second class of monomers of polyurethane is present in the flexible foam 112, specifically a second list being different from the first list, the second list of recyclable candidate components comprising at least one second recyclable candidate component.

The first class of monomers of polyurethane may comprise isocyanate monomers. Specifically, the first list of recyclable candidate components for the first class of monomers of polyurethane may comprise at least one toluene diisocyanate isomer.

As can be seen in FIG. 2, the method may further comprise, if it is determined in the first determination step that the first chemical compound of the first list of recyclable candidate components is not present in the flexible foam 112, generating at least one item of information indicating that the flexible foam 112 is not recyclable (denoted by reference number 130). Alternatively, if it is determined that the first chemical compound of the first list of recyclable candidate components is present in the flexible foam 112, the method may further comprise the following step:

- iii. (denoted by reference number 132) performing the second determination step.

As outlined above, the second determination step comprises determining whether the at least one second chemical compound of the predetermined second list of recyclable candidate components for the second class of monomers of polyurethane is present in the flexible foam 112. The second class of monomers of polyurethane may comprise polyol monomers. Specifically, the second list of recyclable candidate components for the second class of monomers of polyurethane may comprise at least one polyol selected from the group consisting of: polyetherpolyols, polyesterpolyols.

For example, the second determination step may comprise determining whether at least one standard polyol monomer is present in the flexible foam 112.

After performing the second determination step, the method may further comprise:

iv. (denoted by reference number 134) at least one second decision step, comprising automatically deciding, after performing step iii., on the basis of the outcome of step iii., if a third determination step is required, the third determination step comprising determining whether at least one flame retardant compound of a predetermined third list of candidate flame retardant components is present in the flexible foam 112, the third list of candidate flame retardant components comprising at least one flame retardant candidate component.

Thus, if it is determined in the second decision step that the second chemical compound of the second list of recyclable candidate components is not present in the flexible foam 112, the method may comprise generating at least one item of information indicating that the flexible foam 112 is not recyclable (denoted by reference number 136). Alternatively, if it is determined that the second chemical compound of the second list of recyclable candidate components is present in the flexible foam 112, the method may further comprise the following step:

v. (denoted by reference number 138) performing the third determination step.

The third list of candidate flame retardant components may specifically comprise at least one flame retardant component selected from the group consisting of: melamine derivatives, phosphates, derivatives of phosphoric acid, derivatives of phosphonic acid and derivatives of phosphinic acid.

As further shown in FIG. 2, after the third determination step, the method may further comprise:

vi. (denoted by reference number 140) at least one third decision step, comprising automatically deciding, after performing step v., on the basis of the outcome of step v., if a fourth determination step is required, the fourth determination step comprising determining the content of at least one filler compound of a predetermined fourth list of candidate filler compounds in the flexible foam 112, the fourth list of candidate filler compounds comprising at least one candidate filler compound.

Further, if it is determined in the third decision step that the at least one flame retardant compound of the third list of candidate flame retardant components is not present in the flexible foam 112, the method may comprise generating at least one item of information indicating that the flexible 112 foam is not recyclable (denoted by reference number 142). Alternatively, if it is determined that the at least one flame retardant compound of the third list of candidate flame retardant components is present in the flexible foam 112, the method may further comprise the following step:

vii. (denoted by reference number 144) performing the fourth determination step.

The fourth list of candidate filler compounds may specifically comprise at least one filler compound selected from the group consisting of: polymers prepared using one or more olefinic monomers such as acrylonitrile, styrene, (meth)acrylates, (meth)acrylic acid and/or acrylamide.

The content of the at least one filler compound may be compared with at least tolerance level (denoted by reference number 146). The method may comprise, if the content exceeds the tolerance level, generating at least one item of information indicating that the flexible foam 112 is not recyclable (denoted by reference number 148). Alternatively, if the content does not exceed the tolerance level, the method may comprise generating at least one item of information indicating that the flexible foam 112 is recyclable (denoted by reference number 150).

Figure 3A:
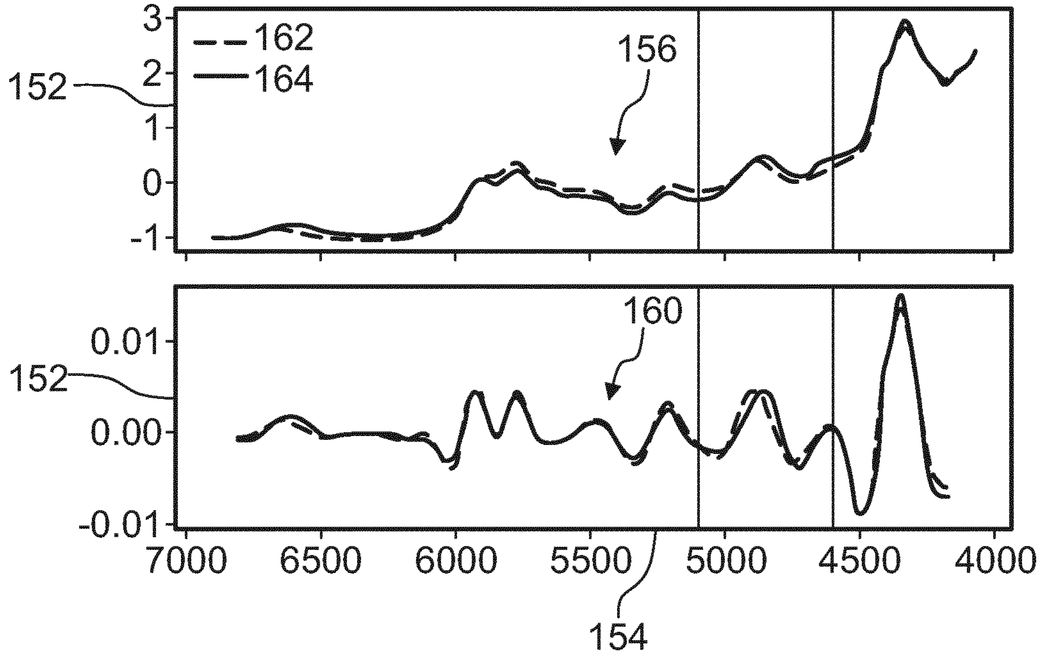
FIGS. 3A and 3B show exemplary spectral data.
Figure 3B:
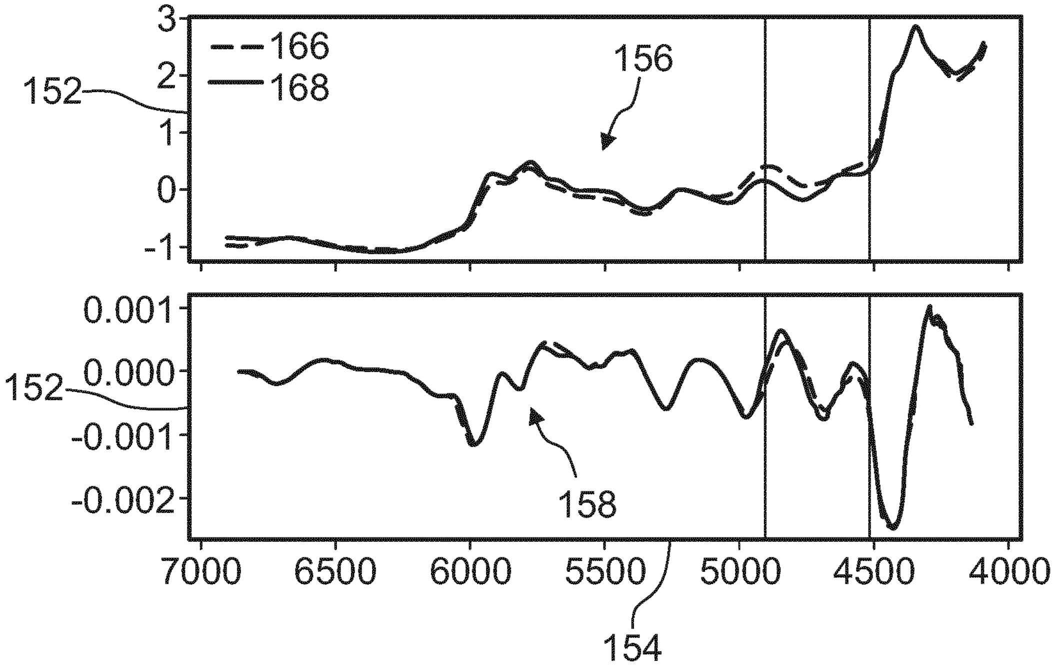

In FIGS. 3A and 3B, exemplary spectral data of the flexible foam 112 are shown. Specifically, FIG. 3A shows exemplary spectral data of the flexible foam 112 for specific polyol monomers. FIG. 3B shows exemplary spectral data of the flexible foam 112 for specific isocyanate monomers. The spectral data may be obtained using a spectrometer device 120, specifically the spectrometer device 120 as schematically shown in FIG. 1. In the FIGS. 3A and 3B, a preprocessed absorbance 152 of the flexible foam 112 is shown as a function of the wavenumber 154 in units of 1/cm. The pre-processing of the spectral data may specifically comprise one or more of filtering and/or smoothing the spectrum of the flexible foam 112. The spectral data may specifically comprise the spectrum 156 of the flexible foam 112 as shown in the upper diagrams of FIGS. 3A and 3B. Additionally or alternatively, the spectral data of the flexible foam 112 may comprise a first-order derivate of the spectrum 158 (FIG. 3B) and/or a second-order derivative of the spectrum 160 (FIG. 3A).

FIG. 3A shows specifically spectral data for a flexible foam 112 comprising an HR polyol monomer (denoted by reference number 162) and for a flexible foam 112 comprising a standard polyol monomer (denoted by reference number 164). The spectral data may be compared in an entire measured wavelength range of the spectral data. As can be seen in FIG. 3A, the spectral data of the flexible foams 112 show a pronounced optical difference in a wavenumber range of 5100 to 4600 1/cm. By performing the method, it may be possible to detect these optical differences between flexible foams 112 comprising the different polyol monomers. The spectral data as shown in FIG. 3A may provide reference spectra, specifically second reference spectra of a second flexible reference foam comprising a HR polyol monomer (denoted by reference number 162) and of a second flexible reference foam comprising a standard polyol monomer (denoted by reference number 164), which specifically may be used in step iii. of the method as described with reference to FIG. 2, for comparing the spectral data of the flexible foam 112 with at least one second reference spectrum of at least one second flexible reference foam made at least partially of at least one polyurethane comprising the at least one second chemical compound of the second list of recyclable candidate components.

FIG. 3B shows specifically spectral data for a flexible foam 112 comprising a toluene diisocyanate isomer (denoted by reference number 166) and for a flexible foam 112 comprising a methylene diphenyl diisocyanate isomer (denoted by reference number 168). The spectral data may be compared in an entire measured wavelength range of the spectral data. As can be seen in FIG. 3B, the spectral data of the flexible foams 112 show a pronounced optical difference in a wavenumber range of 4900 to 4500 1/cm. By performing the method, it may be possible to detect these optical differences between flexible foams 112 comprising the different isocyanate monomers. The spectral data as shown in FIG. 3B may provide reference spectra, specifically first reference spectra of a first flexible reference foam comprising a toluene diisocyanate isomer (denoted by reference number 166) and of a first flexible reference foam comprising a methylene diphenyl diisocyanate isomer (denoted by reference number 168), which specifically may be used in step i. of the method as described with reference to FIG. 2, for comparing the spectral data of the flexible foam 112 with at least one first reference spectrum of at least one first flexible reference foam made at least partially of at least one polyurethane comprising the at least one first chemical compound of the first list of recyclable candidate components.

Figure 4:
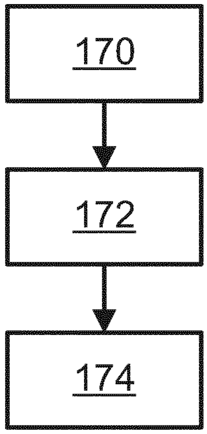
FIG. 4 shows a flow chart of an embodiment of a method of treatment of at least one flexible foam made at least partially of at least one polyurethane.

FIG. 4 shows a flow chart of an exemplary embodiment of a method of treatment of the at least one flexible foam 112 made at least partially of at least one polyurethane. The method may specifically be performed by using the system 114 as described with reference to FIG. 1. The method comprises at least the following steps which, as an example, may be performed in the given order. It shall be noted, however, that a different order is also possible. Further, it is also possible to perform one, more than one or even all of the method steps once or repeatedly. Further, it is possible to perform two or more of the method steps simultaneously or in a timely overlapping fashion. The method may comprise further method steps which are not listed.

The method comprises:

I. (denoted by reference number 170) obtaining spectral data of the flexible foam 112, specifically in the near infrared spectral range;

II. (denoted by reference number 172) obtaining information on the recyclability of the flexible foam 112 by using the by using the spectral data and by using the method of obtaining information on the recyclability of the at least one flexible foam 112 made at least partially of at least one polyurethane according to the present invention, such as according to the embodiment shown in FIG. 2 and/or according to any other embodiment disclosed herein; and III. (denoted by reference number 174) determining, on the basis of the information gained in step III., whether or not to recycle the flexible foam 112 and, if the information indicates a recyclability of the flexible foam 112, at least partially recycling the flexible foam 112.

LIST OF REFERENCE NUMBERS

110 device for obtaining information on the recyclability
112 flexible foam
114 system for treatment of at least one flexible foam
116 mattress
118 retrieving device
120 spectrometer device
122 processor
124 recycling system
126 first determination step
128 first decision step
130 flexible foam is not recyclable
132 second determination step
134 second decision step
136 flexible foam is not recyclable
138 third determination step
140 third decision step
142 flexible foam is not recyclable
144 fourth determination step
146 comparing the filler compound with at least tolerance level
148 flexible foam is not recyclable
150 flexible foam is recyclable
152 pre-processed absorbance
154 wavenumber
156 spectrum
158 first-order derivate of the spectrum
160 second-order derivative of the spectrum
162 spectral data for a flexible foam comprising an HR polyol monomer
164 spectral data for a flexible foam comprising a standard polyol monomer
166 spectral data for a flexible foam comprising a toluene diisocyanate isomer
168 spectral data for a flexible foam comprising a methylene diphenyl diisocyanate isomer
170 obtaining spectral data of the flexible foam
172 obtaining information on the recyclability of the flexible foam
174 determining whether or not to recycle the flexible foam

The invention claimed is:

1. A computer-implemented method of obtaining information on the recyclability of at least one flexible foam made at least partially of at least one polyurethane, the method comprising:

i. at least one first determination step, comprising executing a model trained on a training data set including historical experimental spectral data, the model trained to classify sample spectral data as indicative of one or more constituent compounds, by providing as input to the model spectral data of the flexible foam, wherein output from the model automatically identifies whether at least one first chemical compound of a predetermined first list of recyclable candidate components for a first class of monomers of polyurethane is present in the flexible foam, the first list of recyclable candidate components comprising at least one first recyclable candidate component;

ii. at least one first decision step, comprising automatically deciding, on the basis of the outcome of step i., whether a second determination step is required, iii. performing the second determination step when it is determined in the first determination step that the first chemical compound of the first list of recyclable candidate components is present in the flexible foam, the second determination step comprising determining whether at least one second chemical compound of a predetermined second list of recyclable candidate components for a second class of monomers of polyurethane is present in the flexible foam, the second list of recyclable candidate components comprising at least one second recyclable candidate component, whereas, when it is determined in the first determination step that the first chemical compound of the first list of recyclable candidate components is not present in the flexible foam, the method further comprises generating at least one item of information indicating that the flexible foam is not recyclable, iv. at least one second decision step, comprising automatically deciding, after performing step iii., on the basis of the outcome of step iii., whether a third determination step is required, and v. performing the third determination step when it is determined in the second determination step that the second chemical compound of the second list of recyclable candidate components is present in the flexible foam, the third determination step comprising determining whether at least one flame retardant compound of a predetermined third list of candidate flame retardant components is present in the flexible foam, the third list of candidate flame retardant components comprising at least one flame retardant candidate component, whereas, when it is determined in the second determination step that the second chemical compound of the second list of recyclable candidate components is not present in the flexible foam, the method further comprises generating at least one item of information indicating that the flexible foam is not recyclable.

2. The method according to claim 1, wherein the first class of monomers of polyurethane comprises isocyanate monomers.

3. The method according to claim 1, wherein the model is trained to, in part, compare the spectral data of the flexible foam with at least one first reference spectrum of at least one first flexible reference foam made at least partially of at least one polyurethane comprising the at least one first chemical compound of the first list of recyclable candidate components.

4. The method according to claim 1, wherein the second class of monomers of polyurethane comprises polyol monomers.

5. The method according to claim 1, wherein step iii. comprises comparing the spectral data of the flexible foam with at least one second reference spectrum of at least one second flexible reference foam made at least partially of at least one polyurethane comprising the at least one second chemical compound of the second list of recyclable candidate components.

6. The method according to claim 5, wherein step iii. comprises executing a second model trained on a second training data set including historical experimental spectral data, the second model trained to classify sample spectral data as indicative of one or more constituent compounds, by providing as input to the model the spectral data of the flexible foam, and wherein the second model is trained to, in part, perform said comparing.

7. The method according to claim 6, wherein the second model is the same as the model and the second training data set is the same as the training data set.

8. The method according to claim 1, wherein the third list of candidate flame retardant components comprises at least one flame retardant component selected from the group consisting of: melamine derivatives, phosphates, derivatives of phosphoric acid, derivatives of phosphonic acid, and derivatives of phosphinic acid.

9. The method according to claim 1, wherein step v. comprises comparing the spectral data of the flexible foam with at least one third reference spectrum of at least one third flexible reference foam comprising at least one candidate flame retardant component of the third list of candidate flame retardant components.

10. The method according to claim 1, further comprising:

vi. at least one third decision step, comprising automatically deciding, after performing step v., on the basis of the outcome of step v., if a fourth determination step is required, the fourth determination step comprising determining the content of at least one filler compound of a predetermined fourth list of candidate filler compounds in the flexible foam, the fourth list of candidate filler compounds comprising at least one candidate filler compound.

11. The method according to claim 10, wherein, if it is determined in the third decision step that the at least one flame retardant compound of the third list of candidate flame retardant components is not present in the flexible foam, the method comprises generating at least one item of information indicating that the flexible foam is not recyclable, or else, if it is determined that the at least one flame retardant compound of the third list of candidate flame retardant components is present in the flexible foam, the method further comprises the following step:

vii. performing the fourth determination step.

12. The method according to claim 11, wherein the fourth list of candidate filler compounds comprises at least one filler compound selected from the group consisting of: polymers prepared using one or more olefinic monomers.

13. The method according to claim 11, wherein step vii. comprises comparing the spectral data of the flexible foam with at least one fourth reference spectrum of at least one fourth flexible reference foam comprising at least one candidate filler compound of the fourth list of candidate filler compounds.

14. The method according to claim 11, wherein the fourth list of candidate filler compounds comprises at least one filler compound selected from the group consisting of: polymers prepared using one or more olefinic monomers selected from the group consisting of acrylonitrile, styrene, (meth) acrylates, (meth) acrylic acid, acrylamide, and combinations thereof.

15. A non-transient computer-readable storage medium comprising instructions which, when the instructions are executed by at least one processor, cause the processor to perform the method according to claim 1.

16. A method of treatment of at least one flexible foam made at least partially of at least one polyurethane, the method comprising:

I. obtaining spectral data of the flexible foam;

II. obtaining information on the recyclability of the flexible foam by using the spectral data and by using the method according to claim 1; and III. determining, on the basis of the information gained in step II., whether or not to recycle the flexible foam and, if the information indicates a recyclability of the flexible foam, at least partially recycling the flexible foam.

17. A device for obtaining information on the recyclability of at least one flexible foam made at least partially of at least one polyurethane, the device comprising at least one processor, the processor being configured for performing the method according to claim 1.

18. A system for treatment of at least one flexible foam made at least partially of at least one polyurethane, the system comprising:

A. at least one retrieving device for retrieving spectral data of the flexible foam;

B. at least one device according to claim 17; and

C. at least one recycling system for at least partially recycling the flexible foam.

19. A device for obtaining information on the recyclability of at least one flexible foam made at least partially of at least one polyurethane, the device comprising at least one processor, the processor being configured for performing the method according to claim 16.

20. A system for treatment of at least one flexible foam made at least partially of at least one polyurethane, the system comprising:

A at least one retrieving device for retrieving spectral data of the flexible foam;

B. at least one device according to claim 19; and

C. at least one recycling system for at least partially recycling the flexible foam.

* * * * *